(12) United States Patent
Mannozzi

(10) Patent No.: US 10,952,516 B2
(45) Date of Patent: *Mar. 23, 2021

(54) PROCESS FOR SEMIPERMANENT STRAIGHTENING OF CURLY, FRIZZY OR WAVY HAIR

(71) Applicant: KAO CORPORATION, Tokyo (JP)

(72) Inventor: Alderano Mannozzi, Ascoli Piceno (IT)

(73) Assignee: KAO CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/947,394

(22) Filed: Nov. 20, 2015

(65) Prior Publication Data

US 2016/0073756 A1    Mar. 17, 2016

Related U.S. Application Data

(63) Continuation of application No. 13/810,995, filed as application No. PCT/EP2011/058509 on May 24, 2011, now abandoned.

(30) Foreign Application Priority Data

Jul. 20, 2010 (IT) ................. MC2010A000079

(51) Int. Cl.
| | |
|---|---|
| *A45D 7/06* | (2006.01) |
| *A61K 8/365* | (2006.01) |
| *A61Q 5/04* | (2006.01) |
| *A61K 8/36* | (2006.01) |
| *A61K 8/35* | (2006.01) |

(52) U.S. Cl.
CPC ............. *A45D 7/06* (2013.01); *A61K 8/35* (2013.01); *A61K 8/36* (2013.01); *A61K 8/365* (2013.01); *A61Q 5/04* (2013.01)

(58) Field of Classification Search
None
See application file for complete search history.

(56) References Cited

U.S. PATENT DOCUMENTS

| | | | | |
|---|---|---|---|---|
| 2,390,073 | A * | 12/1945 | Calva .................. | A61K 8/33 132/204 |
| 3,482,581 | A * | 12/1969 | Weigand .............. | A61K 8/345 132/206 |
| 3,793,201 | A * | 2/1974 | Karn ................... | C10M 159/20 252/400.5 |
| 3,910,289 | A | 10/1975 | Wajaroff et al. | |
| 4,752,467 | A | 6/1988 | Konrad et al. | |
| 6,086,861 | A | 7/2000 | Onitsuka et al. | |
| 6,488,920 | B1 * | 12/2002 | Thomas .............. | A61K 8/20 424/70.1 |
| 6,517,822 | B1 | 2/2003 | Buck | |
| 2006/0260632 | A1 * | 11/2006 | Campain ............. | A61K 8/365 132/204 |
| 2009/0165812 | A1 * | 7/2009 | Resnick .............. | A61K 8/33 132/205 |
| 2010/0028280 | A1 | 2/2010 | Philippe et al. | |
| 2010/0300471 | A1 | 12/2010 | Malle et al. | |
| 2011/0256084 | A1 | 10/2011 | Dixon et al. | |
| 2012/0192888 | A1 | 8/2012 | Philippe et al. | |
| 2013/0139844 | A1 | 6/2013 | Malle et al. | |
| 2013/0139845 | A1 | 6/2013 | Malle et al. | |

FOREIGN PATENT DOCUMENTS

| | | |
|---|---|---|
| CA | 1258234 A1 | 8/1989 |
| DE | 198 20 894 A1 | 11/1999 |
| EP | 0 430 406 A2 | 6/1991 |
| EP | 1 900 393 A2 | 3/2008 |
| FR | 1323640 A | 3/1963 |
| FR | 2845903 A1 | 4/2004 |
| FR | 2901472 A1 | 11/2007 |
| GB | 1 416 564 A | 12/1975 |
| JP | 2009-537620 A | 10/2009 |
| KR | 2010-0029567 | 3/2010 |
| SU | 537115 A1 * | 11/1976 |
| WO | WO-2007/135299 A1 | 11/2007 |
| WO | WO-2011/104282 A2 | 9/2011 |
| WO | WO-2012027369 A2 * | 3/2012 ............... A61K 8/23 |
| WO | WO 2012105985 A1 * | 8/2012 ............. A61K 8/447 |
| WO | WO-2012175221 A2 * | 12/2012 ............. A61Q 5/06 |

OTHER PUBLICATIONS chemicaland21.com "glyxoxylic acid," printed 2017; http://chemicalland21.com/industrialchem/organic/GLYOXYLIC%20ACID.htm.*
Bailly "O-Investigation: hair-straightening treatments," from the Oct. 2008 issue of O, The Oprah Magazine and available online Sep. 17, 2008; http://www.oprah.com/style/the-truth-about-hair-straightening-treatments.*
Engineering Tool Box "Density of aqueous solution of inorganic sodium salts," printed 2018; https://www.engineeringtoolbox.com/density-aqueous-solution-inorganic-sodium-salt-concentration-d_1957.html.*
Google translation KR 2010-0013791, printed 2020.*
Gadd et al., "An Apparatus to Investigate the Ironing of Chemically Treated Sheepskins", Journal of the Textile, 1979, vol. 70, Issue 7, pp. 318-320.
International Search Report dated Nov. 4, 2012 issued in connection with International Application No. PCT/EP2011/058509.
Kuratomi, K. et al. "The metabolism of gamma-hydroxyglutamate in rat liver I. Enzymic synthesis of gamma-hydroxy-alpha-ketoglutarate from pyruvate and glyoxylate", Biochimica Et Biophysica Acta, 1963, vol. 78, No. 4, pp. 617-628.
Office Action issued in European App. No. 11721070.8 dated Feb. 20, 2014.

(Continued)

*Primary Examiner* — David J Blanchard
*Assistant Examiner* — Alissa Prosser
(74) *Attorney, Agent, or Firm* — Foley & Lardner LLP

(57) ABSTRACT

A treatment of human hair by means of solutions of Glyoxylic acid that, when used in combination with mechanical straightening by means of hair-straightening irons set at a temperature of approximately 200° C.+/−30° C., allow for the semi-permanent changing of the shape of hair from curly and/or frizzy to straight for at least six consecutive washings with water and shampoo.

4 Claims, No Drawings

(56) References Cited

OTHER PUBLICATIONS

Written Opinion of the International Searching Authority issued in connection with International Application No. PCT/EP2011/059509, dated Jan. 20, 2013.
Translation of SU 537115, Jun. 2013.
CAS Registry entry for "Glyoxylic Acid" accessed 2015.
Machine translation of KR 2010-001379 accessed 2015.
Machine translation of KR 2010-0029567, accessed 2013.

* cited by examiner

PROCESS FOR SEMIPERMANENT STRAIGHTENING OF CURLY, FRIZZY OR WAVY HAIR

This application is a continuation of U.S. application Ser. No. 13/810,995, which in turn is a U.S. National Stage of PCT/EP2011/058509, filed May 24, 2011, and claims priority of Italian Patent Application No. MC2010A000079 filed Jul. 20, 2010. The prior applications are incorporated herein by reference in their entirety.

The present patent application for industrial invention relates to a process used to straighten curly, frizzy or wavy hair semipermanently, which is based on the combined use of glyoxylic acid and a temperature higher than 150° C. The structure of human hair fiber (or hair) is well described in U.S. Pat. No. 6,517,822B1. The techniques that are currently used to straighten curly or frizzy hair can be grouped in three families:

a. Simple treatment with electrical irons basically composed of two hot plates (temperatures higher than 100° C.), between which hair is placed and pressed to obtain desired styling.
b. Chemical treament plus low-temperature mechanical treatment: it uses chemical substances that, after being applied on hair and after treating it at temperatures lower than 100° C., are able to induce modifications in the aspect of hair.
c. Chemical treatment plus high-temperature mechanical treatment: it uses chemical substances that are applied on hair to treat it at temperatures higher than 100° C. Such a technique is able to induce hair modifications that are more considerable than the ones obtained with technique (a) due to the combined action of heat and chemical substances applied to hair.

Numerous chemical substances are currently used to straighten frizzy or curly hair, which are able to interact with bisulphide bridges of cysteine or with peptidic bonds of aminoacids that compose hair. These treatments are well described, for instance, in WO 2007/135299 and US 2010/0300471. In the majority of cases, the substances used for this type of treatments are impaired by problems of high toxicity for man and/or high aggression for hair (i.e. formaldehyde, glutaraldehyde, sodium hydroxide, ammonia, sulphur compounds, guanidine, etc.).

FR 1 323 640 discloses a hair straightening composition that contains Vaseline® and vegetal resins and also rhodinol to avoid hair breakage and ionone and coumarin to perfume.

FR 2 845 903 discloses a hair straightening composition that contains bisulphilketone.

These documents do not disclose any hair straightening process and do not describe the synergic effect of compositions as heating means.

EP 1 900 393 discloses the use of a dione, in particular diacetyl, to improve hair dying and reduce irritation caused by dyes.

DE 198 20 894 discloses a dye that contains tiobarbituric acid and carbonyl compounds, such as diacetyl.

These documents do not disclose that the dye has a hair straightening effect.

Moreover, an expert of the field has no incentive in using a dye with irons to straighten hair.

Numerous patent documents refer to the use of glyoxylic acid in hair treatment to improve the visual aspect and physical-mechanical features of hair.

GB 1416564 uses mercaptoderivatives to obtain permanent hair deformation based on the principle of breakage of cystine disulphide bridges using also glyoxilyc acid salts (not glyoxylic acid) in the mixture with evident purpose of pH buffering agents. The declared concentrations of glyoxylic acid salts are all lower than 4% by weight and moreover the process disclosed in GB 1416564 excludes the use of temperatures higher than 150° C. Such low glyoxylic acid concentrations and such temperatures are not effective for hair straightening.

U.S. Pat. No. 6,086,861 uses glyoxylic acid and its salts to treat hair dandruff.

WO 2007/135299 and FR 2901472 disclose a method to treat keratin fibers using high temperature and special families of carboxylic acids (alpha-hydroxylic and alpha-ketone acids) and derivatives, and in particular pyruvic acid. Moreover, the concentration ranges of pyruvic acids (2-8 Molar) are excessively high, making the acid ineffective in the following hair washings.

The purpose of the present invention is to eliminate the drawbacks of the prior art, by disclosing a hair straightening process that is efficient, effective and time-lasting for at least six washings.

Another purpose of the present invention is to provide such a hair straightening process that is not harmful for hair and for the health of the person applying it.

These purposes are achieved according to the invention, with the characteristics disclosed in the attached independent claim 1.

Advantageous embodiments are disclosed in the dependent claims.

The object of the invention is a process based on the combined use of glyoxylic acid and a high-temperature mechanical treatment. Said mechanical treatment provides for mechanical straightening with iron at a temperature of about 200° C. (+/−30° C.).

More precisely, the process comprises the following steps:
  application of aqueous solution of glyoxylic acid on hair;
  permanence of said substance in contact with hair for a time included from 30 to 120 minutes;
  hair drying;
  hair straightening with hair-straightening iron at a temperature of approximately 200+/−30 C. °.

Unlike the precepts of the prior art, the process of the invention allows for obtaining straight, soft, glossy hair (with strong volume reduction in case of frizzy hair) from curly and/or frizzy hair, maintaining such properties also after repeated washings with water and shampoo (semipermanent effect).

The process of the invention modifies the spatial conformation of hair, reducing volume and number of curves.

Glyoxylic acid is dissolved in water to obtain an aqueous solution of glyoxylic acid. Advantageously, glyoxylic acid is dissolved in water with concentration comprised between 4.5 and 14.5% by weight. Said range has given the best results in terms of efficiency to obtain straight hair.

Advantageously, the aqueous solution of glyoxylic acid can be added with a mixture of Diacetyl and Acetoin. The addition of said mixture has given remarkable effects in terms of hair straightening. In particular, the mixture of Diacetyl and Acetoin is dissolved in said aqueous solution of glyoxylic acid in concentration comprised between 1 and 5% by weight.

Moreover, the aqueous solution of glyoxylic acid can be dissolved in a cosmetic hair composition containing one or more ingredients that are commonly used in cosmetics. For instance, said cosmetic ingredients can be the ones describes in the *Decision of the European Commission* dated 8 May 1996 published on the *Official Journal of the European Community* (GUCE L 132 dated Jan. 6, 1996).

The process of the invention allows for changing the conformation of hair so that it acquires a straight shape, if originally curly and frizzy, and maintains it for at least six hair washings.

In particular, said process has proved to induce semipermanent modifications in hair conformation, which remain such also after repeated hair washings in common use conditions.

Additional characteristics of the invention will appear more evident from the following detailed description that refers to merely illustrative, not limiting embodiments, illustrated in the enclosed drawings and tables.

Experimental tests were carried out consisting in dissolution of Glyoxylic acid in water in ponderal ratio comprised between 4.5 and 14.5% by weight. Following are composition examples of aqueous solutions of glyoxylic acid used for the tests.

EXAMPLE 1

| Water | 95.5 grams |
|---|---|
| Glyoxylic Acid | 4.5 grams (0.6 Molar) |

EXAMPLE 2

| Water | 90 grams |
|---|---|
| Glyoxylic Acid | 10 grams (1.35 Molar) |

EXAMPLE 3

| Water | 85.5 grams |
|---|---|
| Glyoxylic Acid | 14.5 grams (1.9 Molar) |

These solutions were placed in contact with hair that had been previously washed with shampoo according to common use.

Said solutions were then applied on hair with a rigid bristle brush.

Hair was covered with a plastic cap to reduce water evaporation, left in contact with said solutions for 30, 60, 120 minutes, and then dried with hair dryer according to common use. In some embodiments, hair is left in contact with said solution for approximately 60 minutes.

Once dry, hair was straightened with hair-straightening iron heated at average temperature of approximately 210° C.

Finally, hair was washed with shampoo and dried.

At the end of treatment, hair was shiny, straight, soft to touch, with a particularly pleasant general aspect.

Experimental tests were carried out on hair straightening effect that evaluate the reduction of curves and volume in hair.

In particular, comparative tests were carried out, comparing the straigthening effect after mechanical action/heat of irons obtained by putting hair in contact with:
 water only
 compositions according to the present invention;
 a known composition, such as the composition described in example 3 of WO 2007/135299.

To that purpose, the solution described in example 3 of WO 2007/135299 was prepared, consisting in a solution of pyruvic acid 4 Molar (35.2% by weight) in water. Said solution was used according to the instructions contained in WO 2007/135299, that is hair temperature of 40° C., 25 minute contact time and iron temperature of 180°.

The results of the tests are shown in the enclosed tables 1 to 5.

Said tests were carried out with different contact time of the solution with hair. Tables 1 to 4 show the results obtained with the composition of the invention for 60 minute contact time. Instead, table 5 shows the results obtained with the composition of the invention for 30 and 120 minute contact time.

Additional tests were carried out to see whether the effect obtained with solutions of glyoxylic acid could be replicable also when the solution of glyoxylic acid was added to a commercial cosmetic formulation (i.e. substances that are normally used in the cosmetic sector).

To that end an additional test was carried out on a composition of the invention by adding a solution of Glyoxylic acid with a cosmetic found on the market for hair treatment. In particular, a hair straightening test was carried out using a cosmetic product found on the market (Crema Balsamo BALM produced by Tricobiotos spa Vaiano (PO)—Italy), without semipermanent hair straightening effect.

80 grams of said cosmetic product were added to 20 grams of aqueous solution of Glyoxylic acid at 50% by weight.

After carrying out the same hair treatment operations described in the previous pages, results similar to the ones obtained in the tests that were carried out using the same solution of example 2 of the invention were obtained.

As shown in the tables, all tested compositions have a higher straightening effect compared to the simple use of water and hair straightening iron. In particular, the method described in WO 2007/135299 has proved to achieve satisfactory results only for the first four washings, and afterwards hair resumed its original shape (curly and frizzy).

Instead, with the method of the invention, a remarkable result was obtained at the end of the hair treatment: hair was shiny, straight, soft to touch, with a generally pleasant aspect that was maintained also after six consecutive washings with water and shampoo.

The efficacy of the treatment of the invention, in the modification of the shape of hair, has proved to be stable aver time for at least six washings, rinsings and dryings in common use conditions of hair shampoo.

As shown in tables 1-5, the method of the invention has given the best results with the solution of glyoxylic acid described in example 2 for 60 minute contact time on hair.

Better results were even achieved by adding the aqueous solution of glyoxylic acid to a mixture of Diacetyl and Acetoin, in ponderal ratio between 1 and 5% with respect to the total aqueous solution.

The ponderal ratio between Diacetyl and Acetoin can change according to the purity of substances. For illustrative purposes, 1:10, 1:1 and 10:1 diacetyl/acetoin ponderal ratios were considered in examples 4, 5 and 6. Following are composition examples of some of the mixtures used for the tests.

EXAMPLE 4

| Water | 86 grams |
|---|---|
| Glyoxylic acid | 10 grams |
| Diacetyl/Acetoin mixture in 1:10 ratio | 4 grams |

EXAMPLE 5

| Water | 86 grams |
|---|---|
| Glyoxylic acid | 10 grams |
| Diacetyl/Acetoin mixture in 1:1 ratio | 4 grams |

EXAMPLE 6

| Water | 86 grams |
|---|---|
| Glyoxylic acid | 10 grams |
| Diacetyl/Acetoin mixture in 10:1 ratio | 4 grams |

Also in this case, a comparison was made with the method described in example 3 of WO 2007/135299.

Additional tests were carried out to see whether the effect obtained with the aforementioned mixtures could be replicable also in the case when the mixtures were added to a cosmetic formulation.

So, an additional test was carried out by adding a cosmetic hair treatment found on the market to glyoxylic acid and Acetoin and Diacetyl mixture. In particular, a hair straightening test was carried out using a cosmetic product found on the market (Easy care relaxing conditioner produced by Unicompany spa Rome-Italy), without semipermanent hair straightening effect.

76 grams of said cosmetic were added to 20 grams of aqueous solution of Glyoxilyc acid at 50% by weight and 4 grams of Diacetyl/Acetoin mixture in 1/1 weight/weight ponderal ratio.

After carrying out the same hair treatment operations described in the previous pages, the same results obtained in the tests that were carried out using the same solution as example 2 of the invention (Water+Glyoxylic Acid−Diacetyl/Acetoin mixutre in 1/1 ratio (weight/weight)) were obtained.

As shown in tables 5 to 10, at the end of the treatment with addition of Diacetyl and Acetoin mixture, a remarkable result was obtained, which was even better than a solution exclusively containing glyoxylic acid.

Definitions

Glyoxilyc Acid: (CAS number: 563-96-2 or, in aqueous solution, CAS number: 298-12-4). Its use in the cosmetic sector as buffering substance is considered to be safe and is permitted without restrictions.

Diacetyl: (CAS number 431-03-8). It is an organic substance produced by lactic bacteria in presence of carbohydrates and oxygen (see EP0430406). In the production of Diacetyl by means of bacterial fermentation also Acetoin is produced by the same bacteria. Diacetyl is normally used as aroma in the food industry.

Acetoin: (CAS number 513-86-0). It is an organic substance produced by lactic bacteria in presence of carbohydrates and oxygen (see EP0430406). In the production by means of bacterial fermentation of Acetoin, Diacetyl is produced by the same bacteria. Acetoin is normally used as aroma in the food industry.

Mixture: solution composed of Diacetyl and Acetoin in variable ponderal ratio.

Buffering agent: when dissolved in water, it reduces the pH variation of the solution to the addition of acid or alkalinesubstances.

Semipermanent treatment: treatment in acid environment (pH lower than 7) of curly or frizzy hair to straighten it, with permanence in such a condition for at least six washings with water and shampoo, without using substances able to react with cystine disulphide bridges or by means of alkali Permanent treatment: hair treatment to bring it to curly or straight condition with permanence in such a condition for at least six washings by means of oxido-reduction process of disulphide bridges of the cystine contained in hair or by means of hydrolysis of peptidic bonds with alkali (pH higher than 7). The technique is well known and described in WO 2007/135299 A1 and U.S. Pat. No. 4,409,204.

Hair-straightening iron: Electrical heating device that is used by associating heat and pressure to straighten hair. It is generally composed of two flat heating elements, covered with various materials, between which a lock of hair is pressed at a time. Said hair-straightening irons are commonly found on the market.

Hair dryer: ordinary hair-drying device with heating resistance and fan.

TABLE 1

"AFRO" TYPE, NATURAL CURLY HAIR
STRAIGHTENING EFFECT ASSESSMENT (curve reduction)

| TEST PREPARATION | Hair fiber temperature (° C.) | Contact time (minutes) | Temp. of hair straightening iron (° C.) | after no. 1 shampoo and drying | after 2nd shampoo and drying | after 3rd shampoo and drying | after 4th shampoo and drying | after 5th shampoo and drying | after 6th shampoo and drying |
|---|---|---|---|---|---|---|---|---|---|
| WATER 100 ml | 30 | 60 | 210 | (−) | (−) | (−) | (−) | (−) | (−) |
| 95.5 g WATER + 4.5 g GLYOXYLIC ACID | 30 | 60 | 210 | (+++) | (+++) | (++) | (++) | (+) | (+) |
| 90 g WATER + 10 g GLYOXYLIC ACID | 30 | 60 | 210 | (+++) | (+++) | (+++) | (++) | (++) | (++) |
| 85.5 g WATER + 14.5 g GLYOXYLIC ACID | 30 | 60 | 210 | (+++) | (+++) | (+++) | (++) | (++) | (++) |
| 76 g CREMA BALSAMO Tricobiotos + 20 g solution of GLYOXYLIC ACID 50% in water (w/w) | 30 | 60 | 210 | (+++) | (+++) | (+++) | (++) | (++) | (++) |

TABLE 1-continued

"AFRO" TYPE, NATURAL CURLY HAIR
STRAIGHTENING EFFECT ASSESSMENT (curve reduction)

| | | | | | | | | |
|---|---|---|---|---|---|---|---|---|
| PYRUVIC ACID 4 Molar (Example 3 of WO2007/135299 A1) | 40 | 25 | 180 | (+++) | (+++) | (++) | (++) | (+) | (+/−) |

| MEASURED PARAMETER | No effect | Reduction lower than 25% | Reduction between 26 and 50% | Reduction between 51 and 75% | Reduction between 76 and 90% | Reduction >90% |
|---|---|---|---|---|---|---|
| % Reduction of number of curves found in 30 cm of hair (no. of residual curves/no. of initial curves × 100) | − | +/− | + | ++ | +++ | ++++ |

TABLE 2

"AFRO" TYPE, NATURAL CURLY HAIR
VOLUME REDUCTION ASSESSMENT (reduction of hair spatial volume)

| TEST PREPARATION | Hair fiber temperature (° C.) | Contact time (minutes) | Temp. of hair straightening iron (° C.) | after no. 1 shampoo and drying | after 2nd shampoo and drying | after 3rd shampoo and drying | after 4th shampoo and drying | after 5th shampoo and drying | after 6th shampoo and drying |
|---|---|---|---|---|---|---|---|---|---|
| WATER 100 ml | 30 | 60 | 210 | (−) | (−) | (−) | (−) | (−) | (−) |
| 95.5 g WATER + 4.5 g GLYOXYLIC ACID | 30 | 60 | 210 | (+++) | (+++) | (++) | (++) | (+) | (+) |
| 90 g WATER + 10 g GLYOXYLIC ACID | 30 | 60 | 210 | (+++) | (+++) | (+++) | (++) | (++) | (+) |
| 85.5 g WATER + 14.5 g GLYOXYLIC ACID | 30 | 60 | 210 | (+++) | (+++) | (++) | (++) | (++) | (+) |
| 76 g CREMA BALSAMO Tricobiotos + 20 g solution of GLYOXYLIC ACID 50% in water (w/w) | 30 | 60 | 210 | (+++) | (+++) | (+++) | (++) | (++) | (+) |
| PYRUVIC ACID 4 Molar (Example 3 of WO2007/135299 A1) | 40 | 25 | 180 | (+++) | (+++) | (++) | (++) | (+) | (+/−) |

| MEASURED PARAMETER | No effect | Reduction lower than 25% | Reduction between 26 and 50% | Reduction between 51 and 75% | Reduction between 76 and 90% | Riduzione >90 |
|---|---|---|---|---|---|---|
| % Reduction of hair volume (circumference of lock with 1.0 g weight measured at half length) (test final diameter/initial diameter × 100) | − | +/− | + | ++ | +++ | ++++ |

TABLE 3

"European" TYPE, NATURAL CURLY HAIR
STRAIGHTENING EFFECT ASSESSMENT (curve reduction)

| TEST PREPARATION | Hair fiber temperature (° C.) | Contact time (minutes) | Temp. of hair straightening iron (° C.) | after no. 1 shampoo and drying | after 2nd shampoo and drying | after 3rd shampoo and drying | after 4th shampoo and drying | after 5th shampoo and drying | after 6th shampoo and drying |
|---|---|---|---|---|---|---|---|---|---|
| WATER 100 ml | 30 | 60 | 210 | (−) | (−) | (−) | (−) | (−) | (−) |
| 95.5 g WATER + 4.5 g GLYOXYLIC ACID | 30 | 60 | 210 | (++++) | (+++) | (+++) | (++) | (++) | (+) |
| 90 g WATER + 10 g GLYOXYLIC ACID | 30 | 60 | 210 | (++++) | (++++) | (+++) | (+++) | (++) | (++) |
| 85.5 g WATER + 14.5 g GLYOXYLIC ACID | 30 | 60 | 210 | (++++) | (+++) | (+++) | (++) | (++) | (+) |
| 76 g CREMA BALSAMO Tricobiotos + 20 g solution of GLYOXYLIC ACID 50% in water (w/w) | 30 | 60 | 210 | (++++) | (++++) | (+++) | (+++) | (++) | (++) |
| PYRUVIC ACID 4 Molar (Example 3 of WO2007/135299 A1) | 40 | 25 | 180 | (+++) | (+++) | (++) | (++) | (+) | (+/−) |

| MEASURED PARAMETER | No effect | Reduction lower than 25% | Reduction between 26 and 50% | Reduction between 51 and 75% | Reduction between 76 and 90% | Riduzione >90 |
|---|---|---|---|---|---|---|
| % Reduction of number of curves found in 30 cm of hair (no. of residual curves/no. of initial curves × 100) | − | +/− | + | ++ | +++ | ++++ |

TABLE 4

"European" TYPE, NATURAL CURLY HAIR
VOLUME REDUCTION ASSESSMENT (reduction of hair spatial volume)

| TEST PREPARATION | Hair fiber temperature (° C.) | Contact time (minutes) | Temp. of hair straightening iron (° C.) | after no. 1 shampoo and drying | after 2nd shampoo and drying | after 3rd shampoo and drying | after 4th shampoo and drying | after 5th shampoo and drying | after 6th shampoo and drying |
|---|---|---|---|---|---|---|---|---|---|
| WATER 100 ml | 30 | 60 | 210 | (−) | (−) | (−) | (−) | (−) | (−) |
| 95.5 g WATER + 4.5 g GLYOXYLIC ACID | 30 | 60 | 210 | (++++) | (+++) | (+++) | (+++) | (+++) | (++) |
| 90 g WATER + 10 g GLYOXYLIC ACID | 30 | 60 | 210 | (++++) | (++++) | (+++) | (+++) | (++) | (++) |
| 85.5 g WATER + 14.5 g GLYOXYLIC ACID | 30 | 60 | 210 | (++++) | (+++) | (++) | (++) | (++) | (+) |
| 76 g CREMA BALSAMO Tricobiotos + 20 g solution of GLYOXYLIC ACID 50% in water (w/w) | 30 | 60 | 210 | (++++) | (++++) | (+++) | (+++) | (++) | (++) |
| PYRUVIC ACID 4 Molar (Example 3 of WO2007/135299 A1) | 40 | 25 | 180 | (++++) | (+++) | (++) | (++) | (+) | (+/−) |

| MEASURED PARAMETER | No effect | Reduction lower than 25% | Reduction between 26 and 50% | Reduction between 51 and 75% | Reduction between 76 and 90% | Riduzione >90 |
|---|---|---|---|---|---|---|
| % Reduction of hair volume (circumference of lock with 1.0 g weight measured at half length) (test final diameter/initial diameter × 100) | − | +/− | + | ++ | +++ | ++++ |

TABLE 5

"AFRO" TYPE, NATURAL CURLY HAIR
EVALUATION OF STRAIGHTENING EFFECT (reduction of curves) with different contact time

| TEST PREPARATION | Hair fiber temperature (° C.) | Contact time (minutes) | Temp. of hair straightening iron (° C.) | after no. 1 shampoo and drying | after 2nd shampoo and drying | after 3rd shampoo and drying | after 4th shampoo and drying | after 5th shampoo and drying | after 6th shampoo and drying |
|---|---|---|---|---|---|---|---|---|---|
| WATER 100 ml | 30 | 30 | 210 | (−) | (−) | (−) | (−) | (−) | (−) |
| WATER 100 ml | 30 | 120 | 210 | (−) | (−) | (−) | (−) | (−) | (−) |
| 95.5 g WATER + 4.5 g GLYOXYLIC ACID | 30 | 30 | 210 | (++) | (++) | (++) | (++) | (+) | (+/−) |
| 90 g WATER + 10 g GLYOXYLIC ACID | 30 | 30 | 210 | (+++) | (++) | (++) | (++) | (+) | (+) |
| 85.5 g WATER + 14.5 g GLYOXYLIC ACID | 30 | 30 | 210 | (++++) | (++) | (++) | (++) | (+) | (+/−) |
| 76 g CREMA BALSAMO Tricobiotos + 20 g solution of GLYOXYLIC ACID 50% in water (w/w) | 30 | 30 | 210 | (+++) | (+++) | (+++) | (++) | (++) | (+) |
| 95.5 g WATER + 4.5 g GLYOXYLIC ACID | 30 | 120 | 210 | (++++) | (+++) | (+++) | (++) | (++) | (+) |
| 90 g WATER + 10 g GLYOXYLIC ACID | 30 | 120 | 210 | (++++) | (++++) | (++++) | (+++) | (++) | (++) |
| 85.5 g WATER + 14.5 g GLYOXYLIC ACID | 30 | 120 | 210 | (++++) | (++++) | (+++) | (++) | (++) | (+) |
| 76 g CREMA BALSAMO Tricobiotos + 20 g solution of GLYOXYLIC ACID 50% in water (w/w) | 30 | 120 | 210 | (++++) | (++++) | (+++) | (+++) | (++) | (++) |
| PYRUVIC ACID 4 Molar (Example 3 of WO2007/135299 A1) | 40 | 25 | 180 | (++++) | (++++) | (+++) | (+++) | (++) | (+) |

| MEASURED PARAMETER | No effect | Reduction lower than 25% | Reduction between 26 and 50% | Reduction between 51 and 75% | Reduction between 76 and 90% | Riduzione >90 |
|---|---|---|---|---|---|---|
| % Reduction of number of curves found in 30 cm of hair (no. of residual curves/no. of initial curves × 100) | − | +/− | + | ++ | +++ | ++++ |

TABLE 6

"AFRO" TYPE, NATURAL CURLY HAIR
STRAIGHTENING EFFECT ASSESSMENT (curve reduction)

| TEST PREPARATION | Hair fiber temperature (° C.) | Contact time (minutes) | Temp. of hair straightening iron (° C.) | after no. 1 shampoo and drying | after 2nd shampoo and drying | after 3rd shampoo and drying | after 4th shampoo and drying | after 5th shampoo and drying | after 6th shampoo and drying |
|---|---|---|---|---|---|---|---|---|---|
| WATER 100 ml | 30 | 60 | 210 | (−) | (−) | (−) | (−) | (−) | (−) |
| 76 g WATER + 20 g solution of GLYOXILYC ACID 50% in water w/w + 4 g DIACETYL/ACETOIN mixture 1/10 w/w | 30 | 60 | 210 | (++++) | (++++) | (++++) | (+++) | (+++) | (++) |
| 76 g WATER + 20 g solution of GLYOXILYC ACID 50% in water w/w + 4 g DIACETYL/ACETOIN mixture 1/1 w/w | 30 | 60 | 210 | (++++) | (++++) | (++++) | (+++) | (+++) | (+++) |
| 76 g WATER + 20 g solution of GLYOXILYC ACID 50% in water w/w + 4 g DIACETYL/ACETOIN mixture 10/1 w/w | 30 | 60 | 210 | (++++) | (++++) | (++++) | (+++) | (+++) | (+++) |
| 76 g Unicompany COSMETIC BASE + 20 g solution of GLYOXILYC ACID 50% in water w/w + 4 g DIACETYL/ACETOIN mixture 1/10 w/w | 30 | 60 | 210 | (++++) | (++++) | (++++) | (+++) | (+++) | (+++) |
| PYRUVIC ACID 4 Molar (Example 3 of WO2007/135299 A1) | 40 | 25 | 180 | (+++) | (+++) | (++) | (++) | (+) | (+/−) |

| MEASURED PARAMETER | No effect | Reduction lower than 25% | Reduction between 26 and 50% | Reduction between 51 and 75% | Reduction between 76 and 90% | Reduction >90% |
|---|---|---|---|---|---|---|
| % Reduction of number of curves found in 30 cm of hair (no. of residual curves/no. of initial curves × 100) | − | +/− | + | ++ | +++ | ++++ |

TABLE 7

"European" TYPE, NATURAL CURLY HAIR
STRAIGHTENING EFFECT ASSESSMENT (curve reduction)

| TEST PREPARATION | Hair fiber temperature (° C.) | Contact time (minutes) | Temp. of hair straightening iron (° C.) | after no. 1 shampoo and drying | after 2nd shampoo and drying | after 3rd shampoo and drying | after 4th shampoo and drying | after 5th shampoo and drying | after 6th shampoo and drying |
|---|---|---|---|---|---|---|---|---|---|
| WATER 100 ml | 30 | 60 | 210 | (−) | (−) | (−) | (−) | (−) | (−) |
| 76 g WATER + 20 g solution of GLYOXILYC ACID 50% in water w/w + 4 g DIACETYL/ACETOIN mixture 1/10 w/w | 30 | 60 | 210 | (++++) | (++++) | (++++) | (++++) | (++++) | (++++) |
| 76 g WATER + 20 g solution of GLYOXILYC ACID 50% in water w/w + 4 g DIACETYL/ACETOIN mixture 1/1 w/w | 30 | 60 | 210 | (++++) | (++++) | (++++) | (++++) | (++++) | (++++) |
| 76 g WATER + 20 g solution of GLYOXILYC ACID 50% in water w/w + 4 g DIACETYL/ACETOIN mixture 10/1 w/w | 30 | 60 | 210 | (++++) | (++++) | (++++) | (++++) | (++++) | (++++) |
| 76 g Unicompany COSMETIC BASE + 20 g solution of GLYOXILYC ACID 50% in water w/w + 4 g DIACETYL/ACETOIN mixture 1/10 w/w | 30 | 60 | 210 | (++++) | (++++) | (++++) | (++++) | (++++) | (++++) |
| PYRUVIC ACID 4 Molar (Example 3 of WO2007/135299 A1) | 40 | 25 | 180 | (++++) | (+++) | (++) | (++) | (+) | (+/−) |

| MEASURED PARAMETER | No effect | Reduction lower than 25% | Reduction between 26 and 50% | Reduction between 51 and 75% | Reduction between 76 and 90% | Reduction >90% |
|---|---|---|---|---|---|---|
| % Reduction of number of curves found in 30 cm of hair (no. of residual curves/no. of initial curves × 100) | − | +/− | + | ++ | +++ | ++++ |

TABLE 8

"AFRO" TYPE, NATURAL CURLY HAIR
VOLUME REDUCTION ASSESSMENT (reduction of hair spatial volume)

| TEST PREPARATION | Hair fiber temperature (° C.) | Contact time (minutes) | Temp. of hair straightening iron (° C.) | after no. 1 shampoo and drying | after 2nd shampoo and drying | after 3rd shampoo and drying | after 4th shampoo and drying | after 5th shampoo and drying | after 6th shampoo and drying |
|---|---|---|---|---|---|---|---|---|---|
| WATER 100 ml | 30 | 60 | 210 | (−) | (−) | (−) | (−) | (−) | (−) |
| 76 g WATER + 20 g solution of GLYOXILYC ACID 50% in water w/w + 4 g DIACETYL/ACETOIN mixture 1/10 w/w | 30 | 60 | 210 | (++++) | (++++) | (++++) | (++++) | (++++) | (++) |
| 76 g WATER + 20 g solution of GLYOXILYC ACID 50% in water w/w + 4 g DIACETYL/ACETOIN mixture 1/1 w/w | 30 | 60 | 210 | (++++) | (++++) | (++++) | (++++) | (++++) | (+++) |
| 76 g WATER + 20 g solution of GLYOXILYC ACID 50% in water w/w + 4 g DIACETYL/ACETOIN mixture 10/1 w/w | 30 | 60 | 210 | (++++) | (++++) | (++++) | (++++) | (+++) | (++) |
| 76 g Unicompany COSMETIC BASE + 20 g solution of GLYOXILYC ACID 50% in water w/w + 4 g DIACETYL/ACETOIN mixture 1/10 w/w | 30 | 60 | 210 | (++++) | (++++) | (++++) | (+++) | (+++) | (++) |
| PYRUVIC ACID 4 Molar (Example 3 of WO2007/135299 A1) | 40 | 25 | 180 | (+++) | (+++) | (++) | (++) | (+) | (+/−) |

| MEASURED PARAMETER | No effect | Reduction lower than 25% | Reduction between 26 and 50% | Reduction between 51 and 75% | Reduction between 76 and 90% | Reduction >90% |
|---|---|---|---|---|---|---|
| % Reduction of hair volume (circumference of lock with 1.0 g weight measured at half length) (test final diameter/initial diameter × 100) | − | +/− | + | ++ | +++ | ++++ |

TABLE 9

"European" TYPE, NATURAL CURLY HAIR
VOLUME REDUCTION ASSESSMENT (reduction of hair spatial volume)

| TEST PREPARATION | Hair fiber temperature (° C.) | Contact time (minutes) | Temp. of hair straightening iron (° C.) | after no. 1 shampoo and drying | after 2nd shampoo and drying | after 3rd shampoo and drying | after 4th shampoo and drying | after 5th shampoo and drying | after 6th shampoo and drying |
|---|---|---|---|---|---|---|---|---|---|
| WATER 100 ml | 30 | 60 | 210 | (−) | (−) | (−) | (−) | (−) | (−) |
| 76 g WATER + 20 g solution of GLYOXILYC ACID 50% in water w/w + 4 g DIACETYL/ACETOIN mixture 1/10 w/w | 30 | 60 | 210 | (++++) | (++++) | (++++) | (++++) | (++++) | (+++) |
| 76 g WATER + 20 g solution of GLYOXILYC ACID 50% in water w/w + 4 g DIACETYL/ACETOIN mixture 1/1 w/w | 30 | 60 | 210 | (++++) | (++++) | (++++) | (++++) | (++++) | (++++) |
| 76 g WATER + 20 g solution of GLYOXILYC ACID 50% in water w/w + 4 g DIACETYL/ACETOIN mixture 10/1 w/w | 30 | 60 | 210 | (++++) | (++++) | (++++) | (++++) | (++++) | (+++) |
| 76 g Unicompany COSMETIC BASE + 20 g solution of GLYOXILYC ACID 50% in water w/w + 4 g DIACETYL/ACETOIN mixture 1/10 w/w | 30 | 60 | 210 | (++++) | (++++) | (++++) | (++++) | (+++) | (+++) |
| PYRUVIC ACID 4 Molar (Example 3 of WO2007/135299 A1) | 40 | 25 | 180 | (++++) | (+++) | (++) | (++) | (+) | (+/−) |

| MEASURED PARAMETER | No effect | Reduction lower than 25% | Reduction between 26 and 50% | Reduction between 51 and 75% | Reduction between 76 and 90% | Reduction >90% |
|---|---|---|---|---|---|---|
| % Reduction of hair volume (circumference of lock with 1.0 g weight measured at half length) (test final diameter/initial diameter × 100) | − | +/− | + | ++ | +++ | ++++ |

TABLE 10

"AFRO" TYPE, NATURAL CURLY HAIR
EVALUATION OF STRAIGHTENING EFFECT (reduction of curves) with different contact time

| TEST PREPARATION | Hair fiber temperature (° C.) | Contact time (minutes) | Temp. of hair straightening iron (° C.) | after no. 1 shampoo and drying | after 2nd shampoo and drying | after 3rd shampoo and drying | after 4th shampoo and drying | after 5th shampoo and drying | after 6th shampoo and drying |
|---|---|---|---|---|---|---|---|---|---|
| WATER 100 ml | 30 | 15 | 210 | (−) | (−) | (−) | (−) | (−) | (−) |
| WATER 100 ml | 30 | 90 | 210 | (−) | (−) | (−) | (−) | (−) | (−) |
| WATER 100 ml | 30 | 120 | 210 | (−) | (−) | (−) | (−) | (−) | (−) |
| 76 g WATER + 20 g solution of GLYOXILYC ACID 50% in water w/w + 4 g DIACETYL/ACETOIN mixture 1/1 w/w | 30 | 15 | 210 | (+++) | (+++) | (+++) | (++) | (++) | (+) |
| 76 g WATER + 20 g solution of GLYOXILYC ACID 50% in water w/w + 4 g DIACETYL/ACETOIN mixture 1/1 w/w | 30 | 90 | 210 | (++++) | (++++) | (++++) | (++++) | (++++) | (++++) |
| 76 g WATER + 20 g solution of GLYOXILYC ACID 50% in water w/w + 4 g DIACETYL/ACETOIN mixture 1/1 w/w | 30 | 120 | 210 | (++++) | (++++) | (+++) | (++++) | (+++) | (++) |
| 76 g Unicompany COSMETIC BASE + 20 g solution of GLYOXILYC ACID 50% in water w/w + 4 g DIACETYL/ACETOIN mixture 1/10 w/w | 30 | 15 | 210 | (++++) | (++++) | (+++) | (+++) | (++) | (+) |
| 76 g Unicompany COSMETIC BASE + 20 g solution of GLYOXILYC ACID 50% in water w/w + 4 g DIACETYL/ACETOIN mixture 1/10 w/w | 30 | 90 | 210 | (++++) | (++++) | (++++) | (++++) | (+++) | (+++) |
| 76 g Unicompany COSMETIC BASE + 20 g solution of GLYOXILYC ACID 50% in water w/w + 4 g DIACETYL/ACETOIN mixture 1/10 w/w | 30 | 120 | 210 | (++++) | (++++) | (++++) | (+++) | (++) | (++) |
| PYRUVIC ACID 4 Molar (Example 3 of WO2007/135299 A1) | 40 | 25 | 180 | (++++) | (+++) | (++) | (++) | (+) | (+/−) |

| MEASURED PARAMETER | No effect | Reduction lower than 25% | Reduction between 26 and 50% | Reduction between 51 and 75% | Reduction between 76 and 90% | Reduction >90% |
|---|---|---|---|---|---|---|
| % Reduction of number of curves found in 30 cm of hair (no. of residual curves/no. of initial curves × 100) | − | +/− | + | ++ | +++ | ++++ |

The invention claimed is:

1. A process for semi-permanent straightening of human hair, comprising the following steps:
   a) application of aqueous solution of Glyoxylic acid on hair;
   b) permanence of said solution in contact with hair for a time for approximately 60 minutes;
   c) drying of hair with hair-dryer;
   d) hair straightening with hair-straightening iron, set at a temperature of approximately 200° C.; and
   wherein the process is conducted to maintain a pH less than 7, and
   wherein the Glyoxylic acid is dissolved in water in concentration between 4.5 and 10 percent by weight, wherein the process is conducted without substances able to react with cysteine disulphide bridges.

2. The process of claim 1, wherein the hair is covered with a plastic cap during step b).

3. The process of claim 1, wherein step a) further comprises application of a mixture of Diacetyl and Acetoin on hair.

4. The process of claim 3, wherein said mixture of Diacetyl and Acetoin is dissolved in said aqueous solution of Glyoxylic acid in concentration comprised between 1 and 5% by weight.

* * * * *